US008222206B2

(12) United States Patent
Wu et al.

(10) Patent No.: US 8,222,206 B2
(45) Date of Patent: *Jul. 17, 2012

(54) METHOD OF ENHANCING THE MOBILIZATION OF HEMATOPOIETIC STEM CELLS USING TAT-HOXB4H

(75) Inventors: Kou-Juey Wu, Taipei (TW); Chi-Hung Huang, Dayuan Township, Taoyuan County (TW)

(73) Assignee: Taiwan Advance Bio-Pharm Inc., New Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 12/042,097

(22) Filed: Mar. 4, 2008

(65) Prior Publication Data
US 2009/0227496 A1 Sep. 10, 2009

(51) Int. Cl.
*A61P 7/00* (2006.01)
*A61P 37/00* (2006.01)
*A61K 38/00* (2006.01)
(52) U.S. Cl. ............... 514/7.9; 514/13.5; 514/1.1
(58) Field of Classification Search ............ None
See application file for complete search history.

(56) References Cited

U.S. PATENT DOCUMENTS

| 5,837,507 | A | 11/1998 | Largman et al. | |
|---|---|---|---|---|
| 6,303,337 | B1* | 10/2001 | Rothschild et al. | 435/69.1 |
| 2002/0086383 | A1 | 7/2002 | Sauvageau | |
| 2004/0072298 | A1 | 4/2004 | Sauvageau | |
| 2004/0082003 | A1 | 4/2004 | Sauvageau | |
| 2004/0247594 | A1* | 12/2004 | Hunig et al. | 424/144.1 |
| 2008/0014180 | A1 | 1/2008 | Lanza et al. | |
| 2008/0299095 | A1* | 12/2008 | Humphries et al. | 424/93.21 |

FOREIGN PATENT DOCUMENTS

| CN | 101016540 | | 8/2007 |
|---|---|---|---|
| EP | 1889916 | A1 | 2/2008 |
| TW | 094122467 | | 1/2007 |
| TW | 095116399 | | 11/2007 |
| TW | 095132767 | | 3/2008 |
| WO | WO 2005/026196 | | 3/2005 |
| WO | WO 2006/005153 | A1 | 1/2006 |
| WO | WO 2007/090317 | A1 | 8/2007 |

OTHER PUBLICATIONS

Zeidler et al., "Stem cell transplantation in patients with severe congenital neutropenia without evidence of leukemic transformation", Blood 95:1195-1198, 2000.*
Ford et al., "Fusion Tails for the Recovery and Purification of Recombinant Proteins", Prot. Expression Purif. 2:95-107, 1991.*
EMBL Accession No. P17483, Feb. 2007, 3 pages.*
Pombinho et al., Cell Tissue Res. 315:393-406, 2004.*
Basco, Am. J. Trop. Med. Hyg. 75:777-782, 2006.*
Mattis et al. "Purification and Characterization of Bacteriophage P22 Xis Protein," *J. Bacteriol.* 190:5781-5796 (2008).
Rozema, D. and Gellman, S. H. "Artificial Chaperones: Protein Refolding via Sequential Use of Detergent and Cyclodextrin," *J. Am. Chem. Soc.* 117:2373-2374 (1995).
Sauvageau et al. "Overexpression of HOXB4 in hematopoietic cells causes the selective expansion of more primitive populations in vitro and in vivo," *Genes & Development* 9:1753-1765 (1995).
Zuberek et al. "Weak binding affinity of human 4EHP for mRNA cap analogs," *RNA* 13:691-697 (2007).
Saul B. Needleman and Christian D. Wunsch, "III. A general method applicable to the search for similarities in the amino acid sequence of two proteins," Journal of Molecular Biology, 48 (3): 443-453 (1970).
Eugene W. Myers and Webb Miller, "Optimal alignments in linear space," Computer Applied Bioscience, 4 (1): 11-17 (1988).
Christian Buske and R. Keith Humphries, "II. Homeobox genes in leukemogenesis," International Journal of Hematology, 71 (4): 301-308 (2000).
Stuart H. Orkin, "I. Diversification of haematopoietic stem cells to specific lineages," Nature Reviews Genetics, 1 (1): 57-64 (2000).
Steven R. Schwarze, et al., "Protein Transduction: Unrestricted Delivery Into All Cells," Trends in Cell Biology, 10: 290-295 (2000).
Sophie Amsellem et al., "Ex Vivo Expansion of Human Hematopoietic Stem Cells by Direct Delivery of the HOXB4 Homeoprotein," Nature Medicine, 9: 1423-1427 (2003).
Jana Krosl, et al., "In Vitro Expansion of Hematopoietic Stem Cells by Recombinant TAT-HOXB4 Protein," Nature Medicine, 9 (11): 1429-1432 (2003).
Natalia Oganesyan, et al., "On-Column Chemical Refolding of Proteins," PharmaGenomics, 22-25 (2004).
Bruno Nervi, et al., "Cytokines and Hematopoietic Stem Cell Mobilization," Journal of Cellular Biochemistry 99: 690-705 (2006).
Andre Larochelle, et al., "AMD3100 Mobilizes Hematopoietic Stem Cells with Long-Term Repopulating Capacity in Non-human Primates," Blood, 107 (9): 1-38 (2006).
Hal E. Broxmeyer, et al., "Rapid Mobilization of Murine and Human Hematopoietic Stem and Progenitor Cells with AMD3100, a CXCR4 Antagonist," The Journal of Experimental Medicine, 201: 1307-1318 (2008).
Virginia C. Broudy, "Stem cell factor and hematopoiesis", Aug. 15, 1997, Blood 90 (4): 1345-64.
Chi-Hung Huang et al., "Purified Recombinant TAT-Homeobox B4 Expands CD34+ Umbilical Cord Blood and Peripheral Blood Progenitor Cells Ex Vivo", first published online on Aug. 17, 2009, Tissue Engineering Part C: Methods. Jun. 2010, 16(3): 487-496. doi:10.1089/ten.tec.2009.0163.

(Continued)

*Primary Examiner* — David J Steadman
(74) *Attorney, Agent, or Firm* — Finnegan, Henderson, Farabow, Garrett & Dunner LLP

(57) ABSTRACT

The present invention relates to a new and nonobvious method of producing the C-terminal histidine tagged TAT-HOXB4 fusion protein (TAT-HOXB4H), providing unexpected benefits of increased yield and stability to allow for in vivo administration of this protein, and pharmaceutical composition comprising an effective ingredient, TAT-HOXB4H, having stimulatory activity on the production of hematopoietic cells. More specifically, recombinant TAT-HOXB4H protein enhances engraftment of bone marrow transplants, hematopoietic reconstruction, bone marrow re-population and number of circulating stem cells, particularly after chemotherapy or irradiation.

21 Claims, 10 Drawing Sheets

OTHER PUBLICATIONS

Chi-Hung Huang et al., "In Vitro Expansion of Umbilical Cord Blood Stem Cells by Recombination TAT-HOXB4", Mar. 26-27, 2005, Programs and Abstracts, The Twentieth Joint Annual Conference of Biomedical Sciences (2005).

David Kent et al., "Regulation of hematopoietic stem cells by the steel factor/KIT signaling pathway", Apr. 1, 2008, Clinical Cancer Research 14 (7): 1926-30.

Yong Tang et al., "Expansion of haematopoietic stem cells from normal donors and bone marrow failure patients by recombinant hoxb4", first published online on Dec. 17, 2008, British Journal of Haematology 144: 603-612.

Chinese online publication entitled "Technology breakthrough in hematopoietic stem cell proliferation and anti-cancer protein—new opportunity for cancer treatment", website ssttpro.acesuppliers.com/news/new_1.asp?newsid=11277; Jul. 4, 2005; 2 pages; published online by ARCO Infocomm, Inc.

Simpson, Stabilization of Proteins for Storage, Cold Spring Harb Protoc, doi:10.1101/pdb.top79 (2010).

"Centricoe® Centrifugal Filter Devices," Millipore Corporation (2000) 32 pages.

Alter B. P, "Aplastic Anemia, Pediatric Aspects," The Oncologist (1996) 1: 361-366.

Gratwohl A. et al.,"Hematopoetic stem cell transplantation for solid tumor in Europe," Annals of oncology (2004) 15: 653-660.

Hsiao C.-C. et al., "Inflammatory pseudotumor of the liver in Kostmann's disease," Pediatr Surg Int (1999) 15: 266-269.

Lu S-J et al., "Recombinant HoxB4 Fusion Proteins Enhance Hematopoietic Differentiation of Human Embryonic Stem Cells," Stem Cells and Development (2007) 16: 547-559.

* cited by examiner pTAT-HOXB4H Sequence

His　　　　　　　　　　　　　　TAT　　　　　　　　　　　Nhel
ATGCACCACCACCACCACCACTACGGCCGCAAGAAACGCCGCCAGCGCCGCCGCGCTAGC
ATGGCTATGAGTTCTTTTTTGATCAACTCAAACTATGTCGACCCCAAGTTCCCTCCATGCGAG
GAATATTCACAGAGCGATTACCTACCCAGCGACCACTCGCCCGGGTACTACGCCGGCGGCC
AGAGGCGAGAGAGCAGCTTCCAGCCGGAGGCGGGCTTCGGGCGGCGCGCGGCGTGCACC
GTGCAGCGCTACGCGGCCTGCCGGGACCCTGGGCCCCGCCGCCTCCGCCACCACCCCCG
CCGCCCCGCCACCGCCCGGTCTGTCCCCTCGGGCTCCTGCGCCGCCACCCGCCGGGGCC
CTCCTCCCGGAGCCCGGCCAGCGCTGCGAGGCGGTCAGCAGCAGCCCCCGCCGCCTCCC　　HOXB4
TGCGCCCAGAACCCCCTGCACCCCAGCCCGTCCCACTCCGCGTGCAAAGAGCCCGTCGTCT
ACCCCTGGATGCGCAAAGTTCACGTGAGCACGGTAAACCCCAATTACGCCGGCGGGGAGCC
CAAGCGCTCTCGGACCGCCTACACGCGCCAGCAGGTCTTGGAGCTGGAGAAGGAATTTCAC
TACAACCGCTACCTGACACGGCGCCGGAGGGTGGAGATCGCCCACGCGCTCTGCCTCTCCG
AGCGCCAGATCAAGATCTGGTTCCAGAACCGGCGCATGAAGTGGAAAAAAGACCACAAGTTG
CCCAACACCAAGATCCGCTCGGGTGGTGCGGCAGGCTCAGCCGGAGGGCCCCCTGGCCGG
CCCAATGGAGGCCCCCGCGCGCTCCTCGAGCACCACCACCACCACCACTGA
His

Figure 3

TAT-HOXB4H Protein Sequence

TAT
MHHHHHHYGRKKRRQRRRASMAMSSFLINSNYVDPKFPPCEEYSQSDY

LPSDHSPGYYAGGQRRESSFQPEAGFGRRAACTVQRYAACRDPGPPPP

PPPPPPPPPPGLSPRAPAPPPAGALLPEPGQRCEAVSSSPPPPPCAQN      HOXB4

PLHPSPSHSACKEPVVYPWMRKVHVSTVNPYAGGEPKRSRTAYTRQQ

VLELEKEFHYNRYLTRRRRVEIAHALCLSERQIKIWFQNRRMKWKKDHKL

PNTKIRSGGAAGSAGGPPGRPNGGPRALLEHHHHHH

Figure 4

METHOD OF ENHANCING THE MOBILIZATION OF HEMATOPOIETIC STEM CELLS USING TAT-HOXB4H

FIELD OF THE INVENTION

The present invention relates to a new and nonobvious method of producing the C-terminal histidine tagged TAT-HOXB4 fusion protein (TAT-HOXB4H) containing at least 6 histidine (SEQ ID NO: 5) residues at the C-terminus. The method of production provides unexpected benefits of increased stability and yield, which allows for successful in vivo administration of this protein.

BACKGROUND OF THE INVENTION

The growing interest in regenerative medicine has fueled the search for organ-specific stem or self-renewing cells. The best studied population of self-renewing cells is the hematopoietic stem cells (HSCs) as they are innovative options for treatment of diseases from cancer to metabolic disease to immunodeficiencies.

The process of blood cell formation whereby red and white blood cells are replaced through the division of HSCs located in the bone marrow is called hematopoiesis. The HSCs have the key properties of being able to self-renew and to differentiate into mature cells of both lymphoid and myeloid lineages. However, the genetic mechanisms responsible for the control of self-renewal and differentiation outcomes of HSC divisions remain largely unknown.

Currently, transplantation of human HSCs from adult bone marrow, mobilized peripheral blood, and umbilical cord blood (UCB) has been used clinically to treat hematopoietic cancers (leukemias and lymphomas) and to aid immune system recovery from high-dose chemotherapy of non-hematopoietic cancers. However, efficient transplantation requires substantial amount of HSCs from different sources and may require expansion.

HSCs can be originated from bone marrow, peripheral blood and UCB. The extraction of bone marrow cells requires surgery and painful procedure, and therefore becomes less favorable approach. Using peripheral blood cells is also a problem because the difficulty of obtaining qualified HSCs from the hematopoiesis compromised patient who suffer from illness or chemotherapy. UCBs are relatively easier obtained and the quality of HSCs is much higher, however, the number of HSCs obtained from this approach is still limited. Cell number from each extraction is sufficient for a child, but may be insufficient for an adult. To overcome this potential problem, a new approach that facilitates HSC proliferation in vitro by intervening stem cell self-renewal process is indeed necessary for HSC transplantation.

It has been indicated that transcription factors play a critical role in the regulation of gene expression and the differentiation in stem cells (Orkin, S. H. *Nature Reviews Genetics* 1, 57-64, 2000). Transcription factor switches various cellular processes through binding to specific gene target, and this regulation also depends on its cellular concentration. A group of transcription factors called DNA binding homeobox (HOX) was previously found to play a major role in embryogenesis. Recently, HOX family is also found to be involved in the development of HSCs (Buske, C. et. al., *J. Hematol.* 71, 301-308, 2000). The regulation of HSC self-renewal by HOX transcription factor was studied by Dr. Guy Sauvageau from the University of Montreal. Sauvageau's group showed that homeobox gene HOXB4 is critical in the regulation of HSC self-renewal for its ability of maintaining HSC population in bone marrow. HOX genes expressed in blood cells was first observed in human and mouse cell lines. Some types of HOX genes are expressed ubiquitously in various cell types, while others are specifically expressed in certain type of cells or certain time points during the development. For example, eight members of human HOXB cluster are expressed in early stage of erythrocyte development. However, HOXB genes such as HOXB4 and HOXB7 are also expressed in T cells and B cells. Sauvageau's group confirmed that nine HOXA, eight HOXB and four HOXC genes are expressed in $CD34^+$ bone marrow cells. Among these $CD34^+$ bone marrow cells, HOXB2, HOXB9 and HOXA10 are most enriched in erythrocyte progenitor cells. However, no HOX genes are expressed in $CD34^-$ cells. Human homeobox B4(HOXB4) gene was recently demonstrated to effectively expand HSCs in a retroviral or recombinant protein form. Recombinant TAT-HOXB4 proteins were used to expand stem cells in the laboratory scale without the risk of retroviral insertion or co-culture with bone marrow stromal cells (See Krosl, J. et al., *Nature Medicine* 9, 1428-1432, 2003). Therefore, HOXB4 protein is regularly used as a stimulant to promote HSCs expansion in vitro (FIG. 1).

Recent evidence indicated that by adding a TAT protein sequence tag at the N-terminus of HOXB4, exogenous HOXB4 can be delivered into the cell. This TAT sequence directs the transportation of HOXB4 from extracellular side into intracellular side. Upon entering the cytosol, HOXB4 can be refolded into its native conformation by chaperon HSP90. TAT-HOXB4 is able to promote HSC proliferation to 2-6 fold (Amsellem, S. et. al., *Nature Medicine* 9, 1423-1427, 2003; Krosl, J. et. al., *Nature Medicine* 9, 1428-1432, 2003). However, the yield of recombinant TAT-HOXB4 protein from *E. coli* by using regular purification procedure is too low.

In an effort to increase the yield of the recombinant TAT-HOXB4 protein, a method of making a TAT-HOXB4H protein with additional six histidine (SEQ ID NO: 5) residues tagged at the C-terminus was developed which resulted in 3-4 fold yield compared to that of the original protein after purification. The resultant recombinant protein (TAT-HOXB4H) contains 6 histidine (SEQ ID NO: 5) residues at the C-terminus. This method was described in detail in the PCT application PCT/CN2006/000646.

It was shown that the recombinant TAT-HOXB4H protein can be used to expand human peripheral blood or UCB stem cells and the expanded stem cells still possess their pluripotency. Furthermore, the stem cells treated with the recombinant TAT-HOXB4H protein incorporated into the bone marrow of nonobese diabetic-severe combined immunodeficiency (NOD-SCID) mice and human leukocytes were detected in peripheral white blood cells, indicating immune and hematopoiesis reconstitution in the mice.

However, recombinant TAT-HOXB4H proteins have never been used before as a stimulator of hematopoiesis in vivo, specifically, to enhance hematopoietic reconstitution, expansion, bone marrow re-population and to increase the number of peripheral circulating stem cells, particularly after chemotherapy or irradiation. Krosl et al. (2003) and Amsellem et al. (2003) were not able to obtain large amounts of highly stable HOXB4 protein to be used in clinical studies to expand HSCs. In the present invention, the total amount of TAT-HOXB4H protein obtained after purification generally ranges from 6-10 mg from a 1 liter culture, while the total amount of TAT-HOXB4 protein obtained after purification from a 1 liter culture using prior art methods generally ranges from 1-2 mg. The pTAT-HA-HOXB4 plasmid used to express the TAT-HOXB4 protein using prior art methods was a gift from Dr. Guy Sauvageau, University of Montreal, Canada. The method of purifying the TAT-HOXB4H protein using the present invention clearly indicates the increased yield of protein necessary for the in vivo administration. Krosl et al. (2003) also reported that most of their TAT-HOXB4 protein was lost after 4 h of incubation in medium with serum. The present invention shows a significantly high stability of TAT-HOXB4H protein even after 4 weeks, which is a key factor for the use of TAT-HOXB4 protein in clinical studies.

SUMMARY OF THE INVENTION

The present invention is based on the new and nonobvious method of producing the TAT-HOXB4H protein with high yield and stability, and on the finding that recombinant TAT-HOXB4H protein, when administered to a subject in need thereof, increase number of HSCs in both the bone marrow and peripheral blood in vivo.

One aspect of the invention relates to a method of producing a TAT-HOXB4H protein. The method comprises: (a) providing a host cell comprising a vector encoding the protein; (b) expressing the protein in the host cell; (c) collecting an impure solution of the expressed protein; (d) purifying the protein from the solution by: (i) applying the solution to a HisTrap column; (ii) washing the HisTrap column; (iii) eluting the partially purified protein from the HisTrap column to form a partially purified protein solution; (iv) applying the partially purified protein solution to a MonoSP column; (v) washing the MonoSP column; (vi) eluting the purified protein from the MonoSP column in denatured form; (e) refolding the eluted denatured protein using hydrophobic compounds by (i) combining the eluted denatured protein and a solution of hydrophobic compounds to form a solution of protein and hydrophobic compounds; (ii) desalting the solution of protein and hydrophobic compounds to obtain a desalted protein and hydrophobic compound solution; (iii) removing the hydrophobic compounds from the desalted protein solution using ultrafiltration.

One aspect of the invention relates to a method for enhancing the mobilization of HSCs from bone marrow to peripheral blood. The method comprises: a) administering an effective amount of a TAT-HOXB4H protein produced by the methods described herein to a subject in need thereof, and b) allowing the TAT-HOXB4H protein to increase the absolute number of hematopoietic stem cells in the bone marrow of the subject thereby enhancing the mobilization of hematopoietic stem cells to the peripheral blood of the subject.

Another aspect of the invention relates to a method for improving the recovery time of a patient having undergone HSC transplantation, irradiation or chemotherapy. The method comprises: a) administering an effective amount of a TAT-HOXB4H protein produced by the methods described herein to a subject in need thereof, and b) allowing the TAT-HOXB4H protein to increase the absolute number of HSCs to the bone marrow of the subject.

One aspect of the invention relates to a pharmaceutical composition for mobilization of HSCs from bone marrow to peripheral blood in a subject in need thereof. The pharmaceutical composition of the invention includes an effective amount of a TAT-HOXB4H protein produced by the methods described herein sufficient to increase the absolute number of HSCs in the bone marrow of the subject thereby enhancing the mobilization of HSCs to the peripheral blood of the subject.

The pharmaceutical composition of the invention may be administered to a patient having undergone autologous HSC transplantation for improving the recovery time after HSC transplantation.

The pharmaceutical composition of the invention may be administered to a granulocyte-colony stimulating factor (G-CSF)-insensitive patient as a substitute for G-CSF for mobilization of HSCs to peripheral blood.

The pharmaceutical composition of the invention may be administered to a HSC donor thereby allowing a sufficient amount of HSCs to be collected for transplantation in a much less invasive procedure from the peripheral blood rather than the bone marrow of said donor.

Another aspect of the invention relates to treatment of diseases caused by inherited HSC deficiency by systemically administering an effective amount of a recombinant TAT-HOXB4H protein produced by the methods described herein or of a pharmaceutical composition comprising the same to a subject suffering from the diseases. The administered recombinant TAT-HOXB4H protein thereby increases the absolute number of HSCs in the bone marrow of the subject.

A further aspect of the invention relates to a method for improving the recovery time after HSC transplantation by systemically administering an effective amount of a recombinant TAT-HOXB4H protein produced by the methods described herein or of a pharmaceutical composition comprising the same to a subject in need thereof.

A still further aspect of the invention relates to a method for enhancing HSC recovery of a patient receiving irradiation or chemotherapy by systemically administering an effective amount of a recombinant TAT-HOXB4H protein produced by the methods described herein or of a pharmaceutical composition comprising the same to a subject in need thereof.

BRIEF DESCRIPTION OF THE FIGURES

The foregoing aspects and advantages of this invention may become apparent from the following detailed description with reference to the accompanying drawings in which:

FIG. 3 represents the DNA sequence (SEQ ID NO: 3) of pTAT-HOXB4H. The additional 6 histidine (SEQ ID NO: 5) residues introduced at the N- and C-termini in pTAT-HOXB4H are underlined and TAT is highlighted.

FIG. 4 shows the protein sequence (SEQ ID NO: 4) of TAT-HOXB4H protein.

DETAILED DESCRIPTION

I. The TAT-HOXB4H Protein

Figure 1:
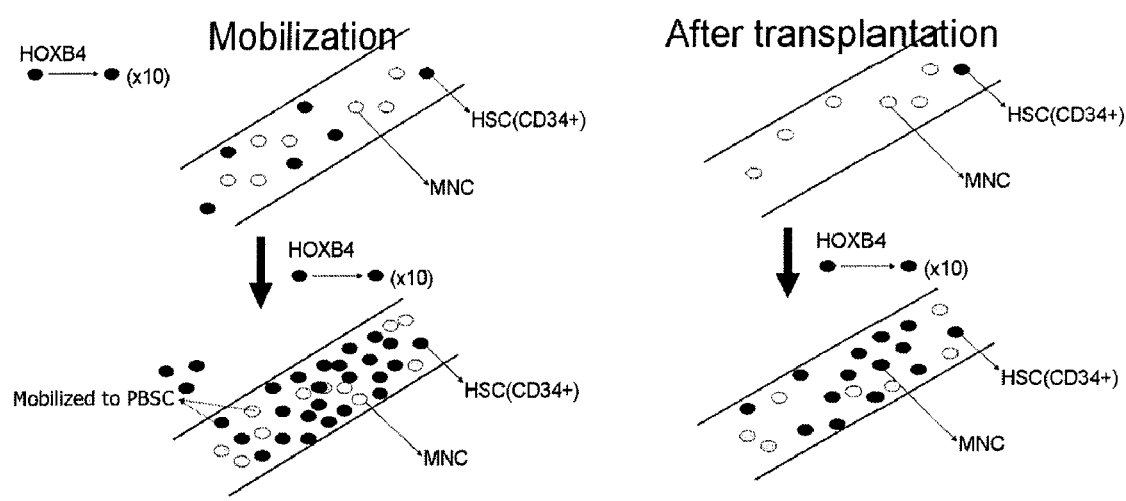
FIG. 1 shows a schematic representation of mobilization of HSCs from CD34 cells to peripheral blood (PB) by in vivo expansion.
Figure 2:
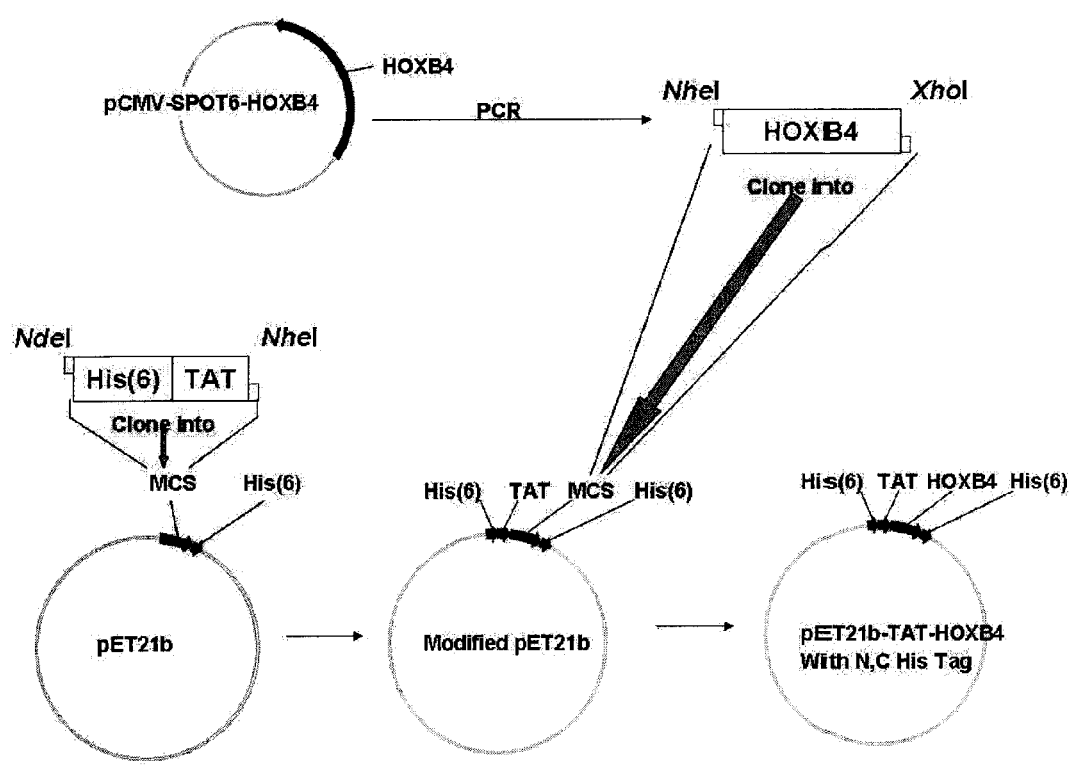
FIG. 2 shows schematic representation of construction and cloning of pTAT-HOXB4H in modified pET21b vector. (The six His tags are disclosed as SEQ ID NO: 5)

The present invention relates to a new and nonobvious method of producing the TAT-HOXB4H protein, providing unexpected benefits of increased stability and yield, which allows for in vivo administration of this protein. The TAT-HOXB4Hprotein is a construct comprising three elements: TAT, HOXB4, and a histidine tag. HOXB4 is a member of the HOX family of transcription factors and promotes HSC expansion. TAT allows the HOXB4 moiety to be transported into the cell. The histidine tag allows for initial increased yield from recombinant expression sources, although the method of production further increases the yield of the protein. pTAT-HOXB4H has been constructed as shown in FIG. 2, and the DNA sequence is shown in FIG. 3. The recombinant TAT-HOXB4H protein refers to a TAT-HOXB4 fusion protein with additional six histidine (SEQ ID NO: 5) residues tagged at the C-terminus (FIG. 4).

Unless otherwise indicated, a protein's amino acid sequence (i.e., its "primary structure" or "primary sequence") may be written from amino-terminus to carboxy-terminus. In non-biological systems (for example, those employing solid state synthesis), the primary structure of a protein (which also includes disulfide (cysteine) bond locations) can be determined by the user.

A "deletion" refers to a change in an amino acid or nucleotide sequence due to the absence of one or more amino acid residues or nucleotides. The terms "insertion" or "addition" refer to changes in an amino acid or nucleotide sequence resulting in the addition of one or more amino acid residues or nucleotides, respectively, to a molecule or representation thereof, as compared to a reference sequence, for example, the sequence found in the naturally occurring molecule. A "substitution" refers to the replacement of one or more amino acids or nucleotides by different amino acids or nucleotides, respectively.

Sequences similar or homologous (e.g., at least about 85% sequence identity) to the sequences disclosed herein are also part of this application. In some embodiment, the sequence identity can be about 90%, 91%, 92%, 93%, 94%, 95%, 96%, 97%, 98%, 99% or higher. Alternatively, substantial identity exists when the nucleic acid segments may hybridize under selective hybridization conditions (e.g., highly stringent hybridization conditions), to the complement of the strand. The nucleic acids may be present in whole cells, in a cell lysate, or in a partially purified or substantially pure form.

Calculations of "homology" or "sequence identity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that may be used if the practitioner is uncertain about what parameters may be applied to determine if a molecule is within a sequence identity or homology limitation of the invention) are a Blossum 62 scoring matrix with a gap penalty of 12, a gap extend penalty of 4, and a frame shift gap penalty of 5. The percent identity between two amino acid or nucleotide sequences can also be determined using the algorithm of E. Meyers and W. Miller (1988) *CABIOS*, 4:11-17) which has been incorporated into the ALIGN program (version 2.0), using a PAM120 weight residue table, a gap length penalty of 12 and a gap penalty of 4.

II. Methods of Making the Recombinant TAT-HOXB4H Protein

A. Cloning and Expression

Systems for cloning and expressing proteins in a variety of host cells are known in the art. Cells suitable for producing proteins are described in, for example, Fernandez et al. (1999) Gene Expression Systems, Academic Press, eds. In brief, suitable host cells include mammalian cells, insect cells, plant cells, yeast cells, or prokaryotic cells, e.g., *E. col*. Mammalian cells available in the art for heterologous protein expression include lymphocytic cell lines (e.g., NSO), HEK293 cells, Chinese hamster ovary (CHO) cells, COS cells, HeLa cells, baby hamster kidney cells, oocyte cells, and cells from a transgenic animal, e.g., mammary epithelial cell. Suitable vectors may be chosen or constructed to contain appropriate regulatory sequences, including promoter sequences, terminator sequences, polyadenylation sequences, enhancer sequences, marker genes, and other sequences. The vectors may also contain a plasmid or viral backbone. For details, see Sambrook et al., Molecular Cloning: A Laboratory Manual, 2nd ed., Cold Spring Harbor Laboratory Press (1989). Many established techniques used with vectors, including the manipulation, preparation, mutagenesis, sequencing, and transfection of DNA, are described in Current Protocols in Molecular Biology, Second Edition, Ausubel et al. eds., John Wiley & Sons (1992).

A further aspect of the disclosure provides a method of introducing the nucleic acid into a host cell. For eukaryotic cells, suitable transfection techniques may include calcium phosphate, DEAE-Dextran, electroporation, liposome-mediated transfection, and transduction using retrovirus or other viruses, e.g., vaccinia or baculovirus. For bacterial cells, suitable techniques may include calcium chloride transformation, electroporation, and transfection using bacteriophage. DNA introduction may be followed by a selection method (e.g., drug resistance) to select cells that contain the nucleic acid.

B. Purification and Refolding

TAT-HOXB4H protein can be initially isolated from the recombinant host cell by any appropriate means known in the art. For example, the protein can be removed from cell supernatant, if the protein is capable of being secreted, or the protein can be removed from a cell lysate.

TAT-HOXB4H protein can be purified using the chromatographic methods comprising: (a) applying the cell lysate or cell supernatant, if the protein is being secreted into the solution, to a HisTrap column; b) washing the HisTrap column with a buffer; (c) eluting the partially purified protein from the HisTrap column (d) applying the partially purified protein obtained from HisTrap column to a MonoSP column; (e) washing the MonoSP column with a buffer; (f) eluting the purified TAT-HOXB4H protein from the MonoSP column.

Cell lysate or cell supernatant, if the protein is capable of being secreted into the solution, can be cleared by centrifugation at 20,000×g for 30 min at 4° C., the supernatant adjusted to 10 mM imidazole and loaded on the HisTrap chelating columns (Amersham Pharmacia). The column can be washed with 8 M urea, 20 mM HEPES, 0.5 mM DTT, 10 mM NaCl, pH 8.0 and 10 mM imidazole to remove unbound proteins. Partially pure TAT-HOXB4 protein can be eluted from the HisTrap column with high concentration of imidazole and salt.

For further purification, partially purified protein obtained from HisTrap column can be applied to MonoSP column (Amersham Pharmacia). The column can be washed with 4 M urea, 20 mM HEPES, 50 mM NaCl, pH 6.5 to remove unbound proteins. Bound TAT-HOXB4H can be eluted with high salt. The purified TAT-HOXB4H protein collected from this purification procedure is in the denatured form.

Further, the denatured TAT-HOXB4H protein eluted from the MonoSP column can be refolded using hydrophobic compounds by (i) combining the eluted denatured protein and a solution of hydrophobic compounds to form a solution of protein and hydrophobic compounds; (ii) desalting the solution of protein and hydrophobic compounds to obtain a desalted protein and hydrophobic compound solution; and (iii) removing the hydrophobic compounds from the desalted protein solution using ultrafiltration.

As used in the present invention, the term "hydrophobic compounds" refer to any hydrophobic compounds capable of protecting the desired protein from forming insoluble aggregates during the denaturing salt-removing step. Hydrophobic compounds suitable for use in the present invention are described in Oganesyan et al., *Pharmagenomics*(2004) 71, 22-26. Suitable hydrophobic compounds include, but are not limited to, Triton X-100, tween-20 or polybenzene compounds. Ultrafiltration or buffer exchange can be carried out by a centricon or stir-cell. The conditions for ultrafiltration or buffer exchange may vary, as recognized by those skilled in the art, depending on the types of the desired protein.

In one embodiment of the present invention, the hydrophobic compound in the desalted solution containing denatured HOXB4H protein is removed by 5-10 times of buffer exchange (each performed by centrifugation at 1000-2500×g for 10 min) with solution containing low to high concentrations of large hydrophobic compounds such as beta-cyclodextrin whereby the denatured HOXB4H protein is refolded into native form thereof.

In one embodiment, purified TAT-HOXB4H protein can be stored in commercially available IMDM (HyClone) medium (storage buffer 1) at 4° C. or −20° C.

In another embodiment, purified TAT-HOXB4H protein can be stored in commercially available DMEM (HyClone) medium (storage buffer 2) at 4° C. or −20° C.

In one embodiment, His tag at the C-terminus of TAT-HOXB4H may be removed before in vivo administration.

In another embodiment His tag at the N-terminus of TAT-HOXB4H can be removed before in vivo administration.

In another embodiment both His tags at the N- and C-termini can be removed before in vivo administration.

C. Preparation of a Pharmaceutical Composition

TAT-HOXB4H may be used as a pharmaceutical composition when combined with a pharmaceutically acceptable carrier. Such a composition may contain, in addition to the TAT-HOXB4H protein and carrier, various diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier may depend on the route of administration.

It is especially advantageous to formulate compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Typical routes of administration include, without limitation, oral, topical, parenteral (e.g., sublingually or buccally), sublingual, rectal, vaginal, and intranasal. The term parenteral as used herein includes subcutaneous injections, intravenous, intramuscular, intrasternal, intracavernous, intrathecal, intrameatal, intraurethral injection or infusion techniques. The pharmaceutical composition is formulated so as to allow the active ingredients contained therein to be bioavailable upon administration of the composition to a patient. Compositions that may be administered to a patient take the form of one or more dosage units, where for example, a tablet may be a single dosage unit, and a container of one or more compounds of the invention in aerosol form may hold a plurality of dosage units.

When a therapeutically effective amount of a TAT-HOXB4H protein is administered orally, the binding agent may be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% binding agent, and preferably from about 25 to 90% binding agent. Examples are sucrose, kaolin, glycerin, starch dextrins, sodium alginate, carboxymethylcellulose and ethyl cellulose. Coloring and/or flavoring agents may be present. A coating shell may be employed. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of the binding agent, and preferably from about 1 to 50% the binding agent.

When a therapeutically effective amount of TAT-HOXB4H protein is administered by intravenous, cutaneous or subcutaneous injection, binding agent may be in the form of a pyrogen-free, parenterally acceptable aqueous solution. The preparation of such parenterally acceptable protein solutions, having due regard to pH, isotonicity, stability, and the like, is within the skill in the art. In some embodiments, pharmaceutical composition for intravenous, cutaneous, or subcutaneous injection may contain, in addition to binding agent an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additive known to those of skill in the art.

In practicing the method of treatment or use of the present invention, a therapeutically effective amount of TAT-HOXB4H protein is administered to a subject, e.g., mammal (e.g., a human). As used herein, the term "therapeutically effective amount" means the total amount of each active component of the pharmaceutical composition or method that is sufficient to show a meaningful patient benefit, e.g., amelioration of symptoms of, healing of, or increase in rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

The amount of TAT-HOXB4H protein in the pharmaceutical composition of the present invention may depend upon the nature and severity of the condition being treated, and on the nature of prior treatments that the patient has undergone, and patient's age and sex. Ultimately, the attending physician may decide the amount of active ingredient with which to treat each individual patient. Initially, the attending physician may administer low doses of active ingredient and observe the patient's response. Larger doses of active ingredient may be administered until the optimal therapeutic effect is obtained for the patient, and at that point the dosage is not generally increased further. It is contemplated that the various pharmaceutical compositions used to practice the method of the present invention may contain about 1 µg to about 1 mg TAT-HOXB4H protein per kg body weight. Examples of dosage ranges that can be administered to a subject can be chosen from: 1 µg/kg to 1 mg/kg, 1 µg/kg to 0.5 mg/kg, 1 µg/kg to 0.1 mg/kg, 10 µg/kg to 0.5 mg/kg, 10 µg/kg to 0.1 mg/kg, 100 µg to 0.5 mg/kg, 250 µg/kg to 0.5 mg/kg. Further, examples of dosage ranges that can be chosen from: 50 µg to 100 mg, 100 µg to 50 mg, 500 µg to 50 mg, 1 mg to 50 mg. The duration of intravenous therapy using the pharmaceutical composition of the present invention may vary, depending on the severity of the disease being treated and the condition and potential idiosyncratic response of each individual patient. In one embodiment, it is contemplated that the duration of each application of the TAT-HOXB4H protein may be in the range of 12 to 24 hours of continuous intravenous administration. In another embodiment, the duration of application of TAT-HOXB4H protein may last as long as patient's radiation or chemotherapy continues. TAT-HOXB4 protein may be administered in the range of 10-100 µg/kg intravenously, twice a day for 4.5 to 5 days. One cycle of the treatment may be enough to expand HSCs in vivo. Ultimately the attending physician may decide on the appropriate duration of intravenous therapy using the pharmaceutical composition of the present invention.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Data obtained from the cell culture assays and animal studies can be used in evaluating a range of dosage for use in humans. The dosage of such compounds may lie within a range of circulating concentrations that include the $ED_{50}$ with little or no toxicity. The dosage may vary within this range depending upon the dosage form employed and the route of administration utilized. The therapeutically effective dose of TAT-HOXB4H can be estimated initially from cell culture assays. A dose may be formulated in animal models to achieve a circulating plasma concentration range that includes the $IC_{50}$ (i.e., the concentration of the test protein which achieves a half-maximal inhibition of symptoms) as determined in cell culture. Levels in plasma may be measured, for example, by high performance liquid chromatography. The effects of any particular dosage can be monitored by a suitable bioassay. Examples of suitable bioassays include, but not limited to, measuring $CD34^+$ stem cells in the mononuclear cell by using fluorescent probe (e.g., FITC) tagged antibodies to CD34+ stem cells and measuring the percentage of LY5 cells in the peripheral blood or bone marrow HSCs by flow cytometry. The polynucleotide and proteins of the present invention are expected to exhibit one or more of the uses or biological activities (including those associated with assays cited herein) identified below. Uses or activities described for proteins of the present invention may be provided by administration or use of such proteins or by administration or use of polynucleotides encoding such proteins (such as, for example, in gene therapies or vectors suitable for introduction of DNA).

III. Methods of Stimulating Hematopoiesis In Vivo

A. Patients in Need of Treatment

The pharmaceutical compositions of the invention may be used to treat diseases which include, but are not limited to, autoimmune disorders, immunodeficiency disorders, and hematological disorders. Additionally, pharmaceutical compositions of the invention may be used to improve the recovery time after HSC transplantation.

The pharmaceutical composition of the invention include, but are not limited to, the treatment of patient suffering from or susceptible to lymphomas, leukemias, Hodgkin's disease and myeloproliferative disorders. Additionally, inherited diseases caused by HSC deficiency and aplastic anemia may be treated by the pharmaceutical composition of the present invention.

Further the pharmaceutical composition of the present invention may be employed to the HSC donors and G-CSF-insensitive patients.

In one embodiment of the invention, TAT-HOXB4H is the only active agent administered for mobilization of HSCs, and fluorouracil (5-FU) is not administered to the donor, either as pretreatment or a combination therapy scheme.

Additional diseases or conditions associated with increased cell survival, that may be treated by the pharmaceutical composition of the invention include, but are not limited to, progression, and/or metastases of malignancies and related disorders such as leukemia (including acute leukemias (for example, acute lymphocytic leukemia, acute myelocytic leukemia (including myeloblastic, promyelocytic, myelomonocytic, monocytic, and erythroleukemia)) and chronic leukemias (for example, chronic myelocytic (granulocytic) leukemia and chronic lymphocytic leukemia)), myelodysplastic syndrome polycythemia vera, lymphomas (for example, Hodgkin's disease and non-Hodgkin's disease), multiple myeloma, Waldenström's macroglobulinemia, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

The present invention is not limited to the particular methodology, protocols, cell lines, animal species or genera, and reagents described below. The terminology used to describe particular embodiments is not intended to limit the scope of the present invention, which may be limited only by the appended claims. As used herein, the singular forms "a," "and," and "the" include plural reference unless the context clearly dictates otherwise. Thus, for example, reference to "a cell" is a reference to one or more cells and includes equivalents thereof known to those skilled in the art.

Unless defined otherwise, all technical and scientific terms used herein have the same meaning as commonly understood to one of ordinary skill in the art to which this invention belongs. Although any methods, devices, and materials similar or equivalent to those described herein can be used in the practice or testing of the invention, the preferred methods, devices, and materials are now described. All publications and patents mentioned herein are hereby incorporated herein by reference for the purpose of describing and disclosing, for example, the constructs and methodologies that are described in the publications which might be used in connection with the presently described invention. The publications discussed above and throughout the text are provided solely for their disclosure prior to the effective date of the present application. Nothing herein is to be construed as an admission that the inventors are not entitled to antedate such disclosure by virtue of prior invention.

Definitions

A "stem cell" is a pluripotent or multipotent cell with the ability to self-renew, to remain undifferentiated, and to become differentiated. Stem cells can divide without limit, at least for the lifetime of the animal in which they naturally reside. Stem cells are not terminally differentiated, i.e., they are not at the end of a pathway of differentiation. When a stem cell divides, each daughter cell can either remain a stem cell or it can embark on a course that leads to terminal differentiation. A "chimeric" stem cell is a stem cell with a portion of its DNA belonging to a heterologous organism.

A "hematopoeitic" cell is a cell involved in the process of hematopoeisis, i.e., the process of forming mature blood cells from precursor cells. In the adult, hematopoeisis takes place in the bone marrow. Earlier in development, hematopoeisis takes place at different sites during different stages of development; primitive blood cells arise in the yolk sac, and later, blood cells are formed in the liver, spleen, and bone marrow. Hematopoeisis undergoes complex regulation, including regulation by hormones, e.g., erythropoietin; growth factors, e.g., colony stimulating factors; and cytokines, e.g., interleukins.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

"Transformation," as used herein, refers to the insertion of an exogenous polynucleotide into a host cell, irrespective of the method used for insertion: for example, transformation by direct uptake, transfection, infection, and the like. For particular methods of transfection, see further below. The exogenous polynucleotide may be maintained as a nonintegrated vector, for example, an episome, or alternatively, may be integrated into the host genome.

In general, the term "protein" refers to any polymer of two or more individual amino acids (whether or not naturally occurring) linked via peptide bonds, as occur when the carboxyl carbon atom of the carboxylic acid group bonded to the α-carbon of one amino acid (or amino acid residue) becomes covalently bound to the amino nitrogen atom of the amino group bonded to the a-carbon of an adjacent amino acid. These peptide bond linkages, and the atoms comprising them (i.e., a-carbon atoms, carboxyl carbon atoms (and their substituent oxygen atoms), and amino nitrogen atoms (and their substituent hydrogen atoms)) form the "polypeptide backbone" of the protein. In addition, as used herein, the term "protein" is understood to include the terms "polypeptide" and "peptide" (which, at times, may be used interchangeably herein). Similarly, protein fragments, analogs, derivatives, and variants are may be referred to herein as "proteins," and shall be deemed to be a "protein" unless otherwise indicated. The term "fragment" of a protein refers to a polypeptide comprising fewer than all of the amino acid residues of the protein. As may be appreciated, a "fragment" of a protein may be a form of the protein truncated at the amino terminus, the carboxy terminus, and/or internally (such as by natural splicing), and may also be variant and/or derivative. A "domain" of a protein is also a fragment, and comprises the amino acid residues of the protein required to confer biochemical activity corresponding to naturally occurring protein.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide.

An "isolated," "purified," "substantially isolated," or "substantially pure" molecule (such as a polypeptide or polynucleotide) is one that has been manipulated to exist in a higher concentration than in nature. For example, a subject protein is isolated, purified, substantially isolated, or substantially purified when at least 50%, 70%, 75%, 80%, 85%, 90%, 91%, 92%, 93%, 94%, 95%, 96%, 97%, 98%, 99% or more of non-subject-protein materials with which it is associated in nature have been removed. As used herein, an "isolated," "purified," "substantially isolated," or "substantially purified" molecule includes recombinant molecules.

A "SCID mouse" is a mouse model for severe combined immunodeficiency syndrome (SCID), which causes severe defects in the development of the immune system. These mice are deficient in, or completely lack, both T and B lymphocytes. The SCID mutation appears to impair the recombination of antigen receptor genes, causing a lack of functional T and B lymphocytes. Other hematopoietic cell types appear to develop and function normally. SCID mice readily support normal lymphocyte differentiation and can be reconstituted with normal lymphocytes from syngeneic or allogeneic mice, or with human lymphocytes. These mice also support the growth of allogeneic and xenogeneic tumors. Therefore, SCID mice, which allow disseminated growth of a number of human tumors, particularly hematologic disorders and malignant melanoma, can be used to investigate malignancies.

The terms "subject," "individual," "host," and "patient" are used interchangeably herein to refer to a living animal, including a human and a non-human animal. The subject may, for example, be an organism possessing immune cells capable of responding to antigenic stimulation, and stimulatory and inhibitory signal transduction through cell surface receptor binding. The subject may be a mammal, such as a human or non-human mammal, for example, dogs, cats, pigs, cows, sheep, goats, horses, rats, and mice. The term "subject" does not preclude individuals that are entirely normal with respect to a disease, or normal in all respects.

The term "treatment" refers to a therapeutic or preventative measure. The treatment may be administered to a subject having a medical disorder or who ultimately may acquire the disorder, in order to prevent, cure, delay, reduce the severity of, or ameliorate one or more symptoms of a disorder or recurring disorder, or in order to prolong the survival of a subject beyond that expected in the absence of such treatment.

The term "therapeutically effective amount" means the amount of the subject compound that may elicit a desired response, for example, a biological or medical response of a tissue, system, animal, or human that is sought, for example, by a researcher, veterinarian, medical doctor, or other clinician.

EXAMPLES

The following specific examples are to be construed as merely illustrative, and not limitative of the remainder of the disclosure in any way whatsoever. Without further elaboration, it is believed that one skilled in the art can, based on the description herein, utilize the present invention to its fullest extent.

Example 1

Construction of Plasmid pET21b-His-pTAT-HOXB4-His (a) The Modification of pET21b Plasmid Containing N- and C-Terminal His Tag and TAT Signal Peptide.

The expression vector pET21b containing N-terminal His tag and a TAT signal peptide was generated by inserting oligonucleotides 5'-TATGCACCACCACCACCACCAC-TACGGCCGCAAGAAACGCCGCCAGCGCCGCCG GCG-3' (sense) (SEQ ID NO: 1) and 5'-CTAGCGGCGCTG-GCGGCGTTTCTTGCGGCC GTAGTGGTGGTGGTG-GTGGTGCA -3' (antisense) (SEQ ID NO: 2) into pET21b plasmid. The C-terminal His-Tag is already present in the pET21b vector.

(b) Cloning of HOXB4 into Modified pET21b Expression Vector

A DNA fragment containing the open reading frame (ORF) of HOXB4 and additional 6 histidine (SEQ ID NO: 5) coding sequence was obtained by PCR amplification using plasmid MGC54130(GeneDiscovery, Taipei, Taiwan. Cat. No. 5533346) as the template, and the PCR-generated HOXB4 cDNA fragment was subcloned into the modified pET21b expression vector. Plasmid construction and nucleic acid sequences are shown in FIGS. 2 and 3.

Example 2

Expression of Recombinant TAT-HOXB4H Protein in E. coli

The pET21b-His-TAT-HOXB4-His expression vector was transformed into *E. coli* strain BL21(DE3)pLysS (Novagen). The transformed cells were grown overnight at 37° C. The overnight-grown cultures were diluted to an initial OD600 of 0.05. The cultures were then grown to an OD600 of 0.5 at 37° C., induced with 1 mM isopropyl-beta-D-thiogalactopyranoside (IPTG) at 37° C. for 3 hr, with vigorous shaking.

Example 3

Purification of Recombinant TAT-HOXB4H Protein

Following induction, cells were harvested by centrifugation and resuspended in Buffer A (8 M Urea, 20 mM HEPES, 0.5 mM DTT and 100 mM NaCl, pH 8.0). The cell suspension was passed three times through a French press, and the cell lysate cleared by centrifugation at 20,000×g for 30 min at 4° C., adjusted the supernatant to 10 mM imidazole and loaded on the HisTrap chelating columns (Amersham Pharmacia). Bound proteins were eluted with 50, 100 and 250 mM imidazole in buffer A. TAT-HOXB4H containing fractions were loaded on a MonoSP column in Buffer B (4 M urea, 20 mM HEPES and 50 mM NaCl, pH 6.5), eluted with 1.5 M NaCl and 20 mM HEPES (pH 8.0).

Example 4

Renaturation of Recombinant TAT-HOXB4H Protein

The TAT-HOXB4H protein in the eluted fractions was solubilized and denatured in a solution containing denaturing salt (e.g., guanidine hydrochloride) and then it was mixed with D-PBS-T buffer (0.1% Triton X-100 in 2× PBS). The ratio of the TAT-HOXB4H protein solution to D-PBS-T buffer was 1:4. The resultant mixture was added to a 10K centricon tube (50 ml or 15 ml) pretreated with water (10 ml or 3 ml), and then centrifuged at 3000 rpm for 10 min. In this step, the denaturing salt is replaced by D-PBS-T buffer in which Triton X-100 is capable of binding with the hydrophobic region of the HOXB4H protein.

This step of ultrafiltration or buffer exchange using 10K centricon was performed ten times with solution containing different concentrations of beta-cyclodextrin (two times of each 1 mM, 2 mM, 3 mM, 4 mM and 5 mM beta-cyclodextrin in storage buffer IMDM by centrifuging at 1000-2500×g for 10 min. The remaining sample in the 10K centricon tube was collected and stored at −80° C.

Figure 5:
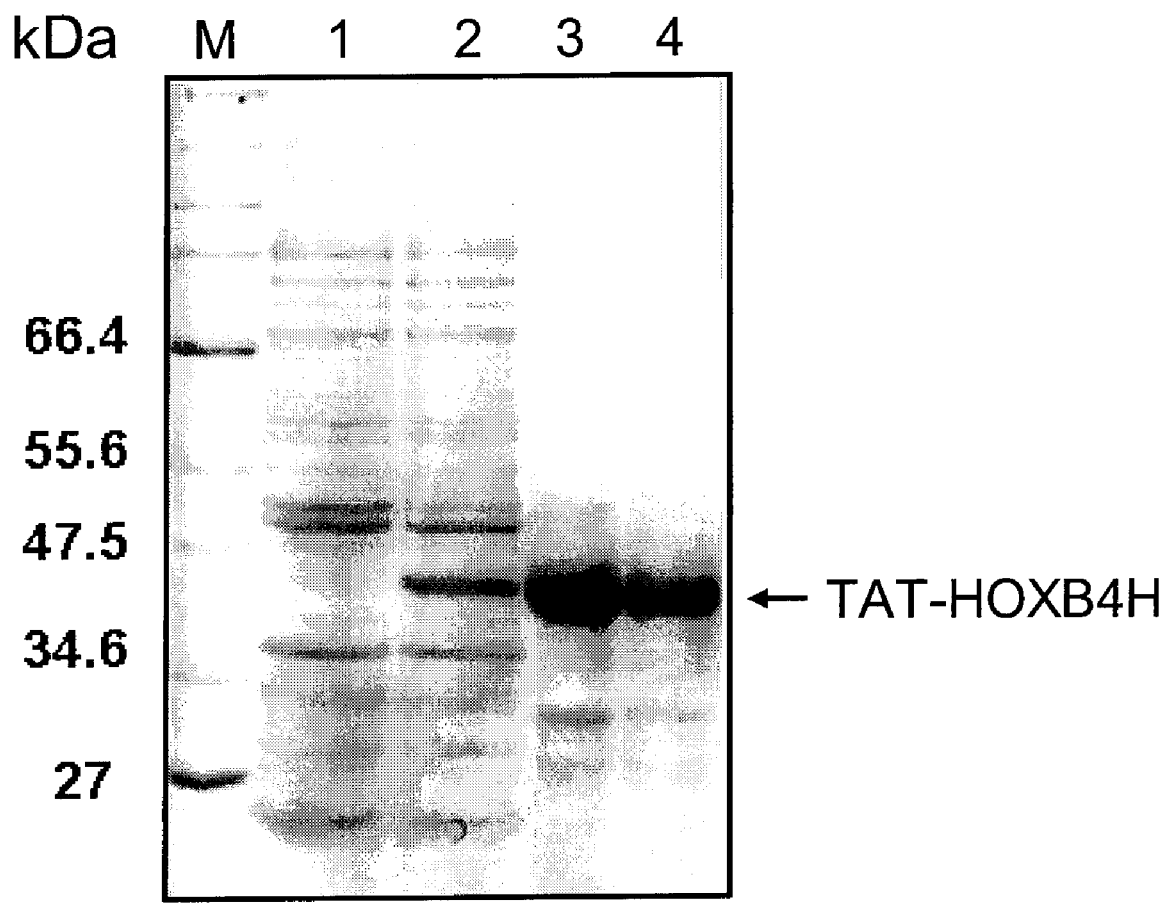
FIG. 5 shows 10% SDS-polyacrylamide gel (1.5 mm) demonstration of the purification of TAT-HOXB4H protein. The SDS-polyacrylamide gel was stained with coomassie blue. Lane 1, molecular weight markers (M), 0.3 µg protein; lane 2, cell lysate from uninduced BL21(DE3)pLysS cells expressing TAT-HOXB4H protein,1 µg protein; lane 3, cell lysate from induced BL21(DE3)pLysS cells expressing TAT-HOXB4H protein with 1 mM IPTG, 1 µg protein; lane 4, purified TAT-HOXB4H, 0.7 mg protein; lane 5, purified TAT-HOXB4(0.2 mg protein). The pTAT-HA-HOXB4 plasmid used to express the TAT-HOXB4 protein (lane 5) was a gift from Dr. Guy Sauvageau, University of Montreal, Canada. Equal volume of fractions, that were collected from MonoSP column, were loaded in the lanes 4 and 5.

Homogeneity of the purified TAT-HOXB4H protein was analyzed by SDS-polyacrylamide gel followed by coomassie staining (FIG. 5). As shown in FIG. 5, TAT-HOXB4H purified from HisTrap and MonoSP resulted in 3-4 fold yield compared to that of the TAT-HOXB4 protein. The pTAT-HA-HOXB4 plasmid was a gift from Dr. Guy Sauvageau, University of Montreal, Canada. This plasmid was transformed into BL21(DE3)pLysS (Novagen) and the purification of TAT-HOXB4 protein was performed as described in Krosl et al, 2003.

Example 5

Stability of Recombinant TAT-HOXB4H Protein

Figure 6:
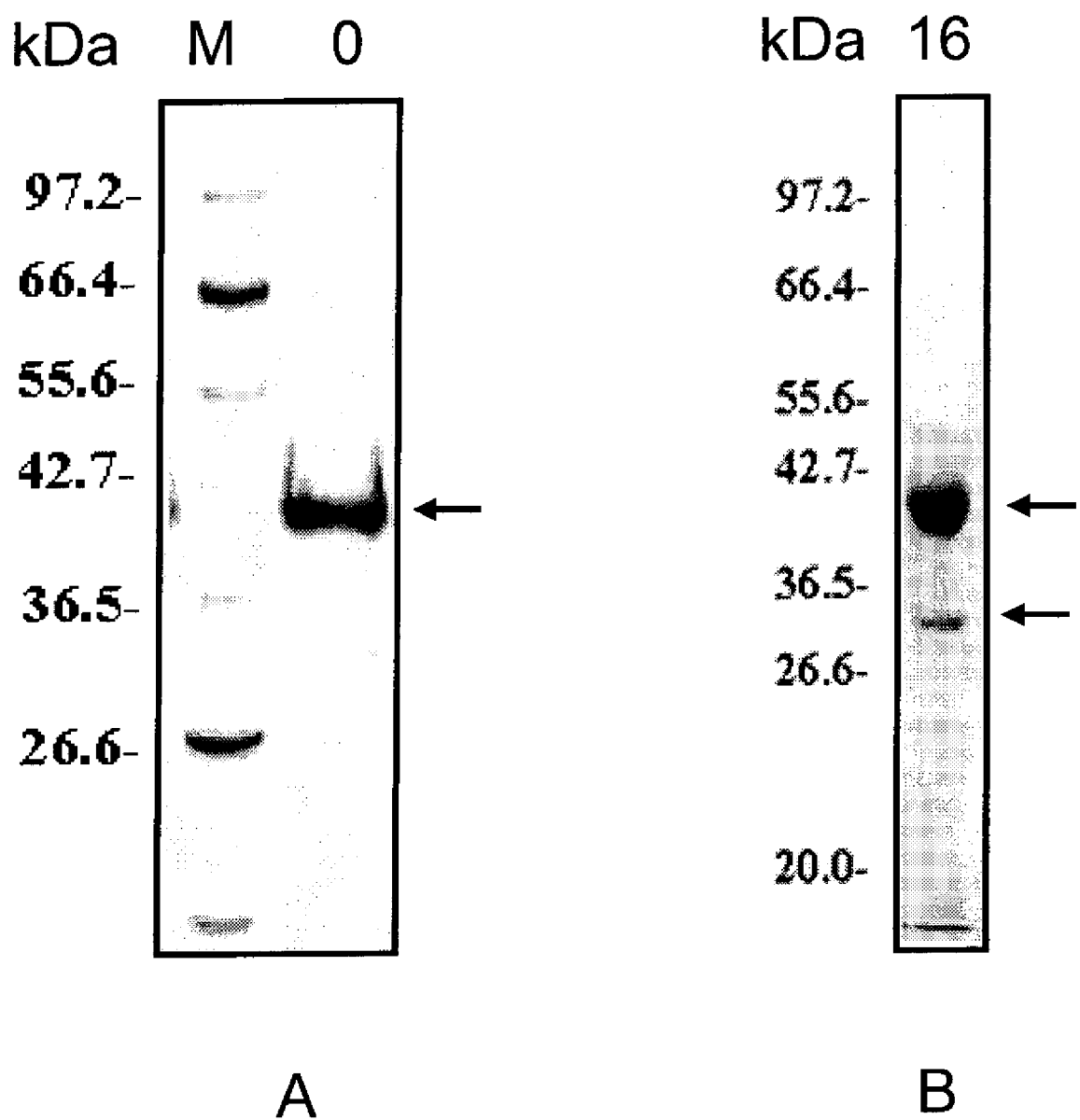
FIG. 6 shows SDS-polyacrylamide gel analysis of the stability of purified TAT-HOXB4H protein stored in PBS for 0 hours (A) and 16 hours (B) at 4° C. M represents molecular weight markers, 0 represents 0 hours incubation at 4° C., 16 represents 16 hour incubation at 4° C.

The Stability of the TAT-HOXB4H was measured by SDS-polyacrylamide gel analysis. Upon storage full length TAT-HOXB4H can be degraded into 30 kD and 10 kD fragments. As shown in FIG. 6, TAT-HOXB4H protein produced by the method of this invention was stable even after 16 hours stored in PBS at 4° C.

Figure 7:
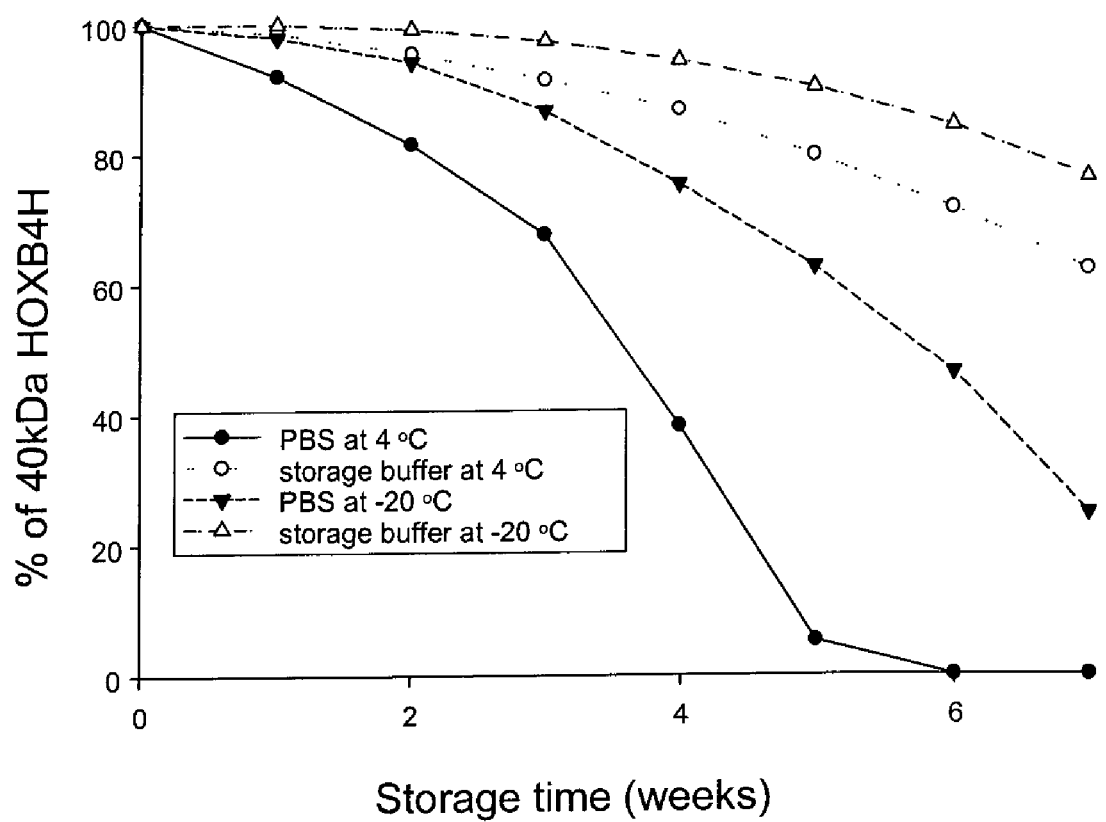
FIG. 7 shows the stability of TAT-HOXB4H protein stored at 4° C. and −20° C. in PBS and storage buffer, IMDM, analyzed by 10% SDS-polyacrylamide followed by coomassie staining. Arrows indicate TAT-HOXB4H protein bands.

Further, the stability of TAT-HOXB4H protein stored at 4° C. and −20° C. in PBS and storage buffer IMDM was analyzed by 10% SDS-polyacrylamide gel electrophoresis followed by coomassie staining. As shown in FIG. 7, when IMDM was used as a storage buffer, the stability of the TAT-HOXB4H protein was maintained even after 4 weeks.

Example 6

Effect of Recombinant TAT-HOXB4H Protein on Hematopoiesis in Wild Type Balb/c Mice Balb/c mice were used to investigate the possible effect of recombinant TAT-HOXB4H protein on mobilization of HSCs from bone marrow to peripheral blood. TAT-HOXB4H recombinant protein in phosphate buffered saline (PBS) was administered by subcutaneous injection four times per day for 4 days. To examine dose-responsiveness, experimental groups (n=21) received a dose ranged from 1 µg, 5 µg, 10 µg, 15 µg . . . to 100 µg per kg BW per mouse. A separate group of control mice received phosphate buffered saline only, and another group of control mice were injected subcutaneously twice per day for 4 day with a dose of 5 µg per kg BW of G-CSF per mouse.

Peripheral blood was harvested from all mice and analyzed by a flow cytometer to obtain the percentage of $CD34^+$ stem cells in mononuclear cell (MNC). The results are reported as the mean±s.d. in Table 1.

TABLE 1

| Group (Experimental/Control) | TAT-HOXB4H (µg/kg) | $CD34^+$/MNC (%) |
| --- | --- | --- |
| 1 | 1 | 0 ± 0.03 |
| 2 | 5 | 0.3 ± 0.05 |
| 3 | 10 | 0.45 ± 0.03 |
| 4 | 15 | 0.42 ± 0.01 |
| 5 | 20 | 0.38 ± 0.05 |
| 6 | 25 | 0.41 ± 0.02 |
| 7 | 30 | 0.35 ± 0.21 |
| 8 | 35 | 0.33 ± 0.11 |
| 9 | 40 | 0.29 ± 0.16 |
| 10 | 45 | 0.46 ± 0.01 |
| 11 | 50 | 0.45 ± 0.02 |
| 12 | 55 | 0.42 ± 0.06 |
| 13 | 60 | 0.44 ± 0.02 |
| 14 | 65 | 0.41 ± 0.04 |
| 15 | 70 | 0.41 ± 0.03 |
| 16 | 75 | 0.49 ± 0.01 |
| 17 | 80 | 0.45 ± 0.04 |
| 18 | 85 | 0.46 ± 0.07 |
| 19 | 90 | 0.44 ± 0.02 |
| 20 | 95 | 0.41 ± 0.01 |
| 21 | 100 | 0.42 ± 0.05 |
| Control (PBS) | 0 | 0.002 |
| Control (G-CSF) | 0 | 0.5 ± 0.03 |

The percentage of $CD34^+$/MNC in peripheral blood harvested from the treated mice is shown in Table 1. The TAT-HOXB4H treated experimental groups 3-21(received a dose of 10 µg or above per kg BW) showed substantially the same mobilization effect as G-CSF treated control group.

Bone marrow from TAT-HOXB4H treated mice (Exp. Group 3 received a dose of 10 µg per kg BW), G-CSF treated mice, and PBS injected mice were further phenotyped using FITC-conjugated antibody to $CD34^+$ (Becton Dickinson) and analyzed by a flow cytometer. Bone marrow from mice treated with TAT-HOXB4H (FIG. 5C) appears to be richer in CD34+ stem cells than bone marrow from G-CSF (FIG. 5A) and PBS (FIG. 5B) injected mice. Therefore, these results indicate that injection of recombinant TAT-HOXB4H proteins results in increased number of HSCs in both the bone marrow and peripheral blood in mice.

Example 7

Effect of Recombinant TAT-HOXB4H Protein on Hematopoiesis in Rhesus Monkey

Male adult rhesus monkeys were used to investigate the efficacy of recombinant TAT-HOXB4H protein in monkeys. Experimental group I (n=5) were injected intravenously with 10 μg per kg BW of recombinant TAT-HOXB4H protein four times per day for 4 days. Experimental group II (n=5) were injected intravenously with 10 μg per kg BW of TAT-HOXB4H four times per day and injected subcutaneously with 5 μg per kg BW of G-CSF for 4 days. Control group I received PBS only, and control group II were injected subcutaneously twice per day for 4 day with a dose of 5 μg per kg BW of G-CSF. Peripheral blood were harvested from all monkeys and analyzed by a flow cytometer to obtain the percentage of CD34+ stem cells in mononuclear cell (MNC). The results are presented in Table 2.

TABLE 2

| Group (Experimental/Control) | CD34+/MNC (%) |
|---|---|
| I. TAT-HOXB4H (10 μg/kg) | 0.62 |
| II. TAT-HOXB4H (10 μg/kg) + G-CSF (5 μg/kg) | 0.38 |
| Control 1 (PBS) | 0.07 |
| Control 2 (G-CSF, 5 μg/kg) | 0.28 |

As shown in Table 2, monkeys (experimental group I) treated with TAT-HOXB4H only showed a significantly better mobilization effect than G-CSF treated monkeys (control group II). The monkeys treated with TAT-HOXB4H and G-CSF (experimental group II) showed a slightly better mobilization effect than G-CSF treated monkeys (control group II).

Bone marrow specimens from monkeys treated with TAT-HOXB4H, G-CSF or PBS were further phenotyped using FITC-conjugated antibody to CD34+ (Becton Dickinson) and analyzed by a flow cytometer. Bone marrow specimens from monkeys treated with TAT-HOXB4H (FIG. 6C) appears significantly richer in CD34+ stem cells than bone marrow specimens from G-CSF (FIG. 6A), TAT-HOXB4H+G-CSF (FIG. 6B) and PBS (FIG. 6D) injected monkeys.

Example 8

Figure 10:
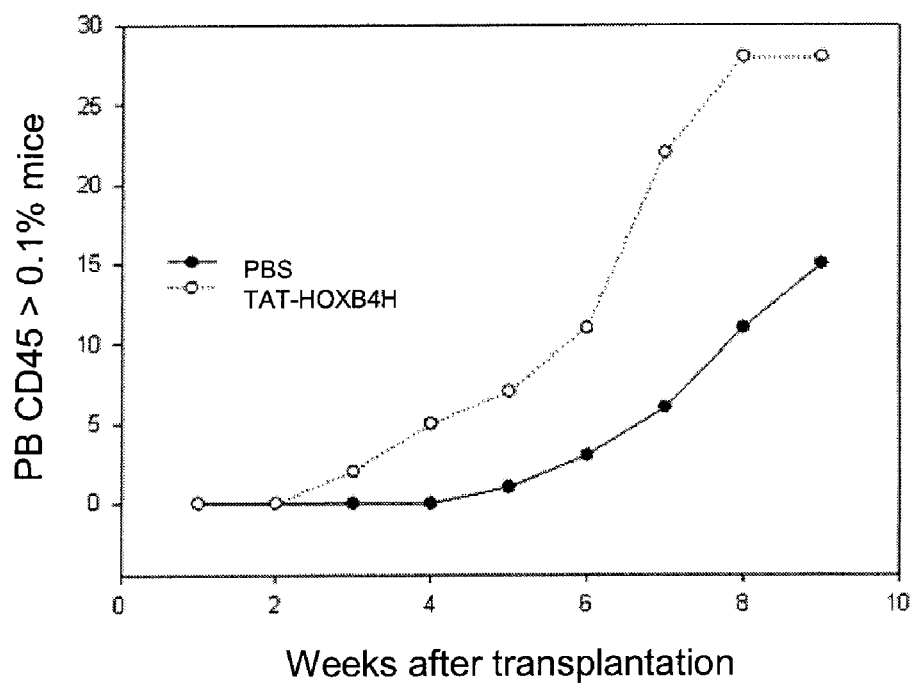
FIG. 10 shows effect of TAT-HOXB4H protein on hematopoietic recovery in NOD-SCID mice.
Figure 11:
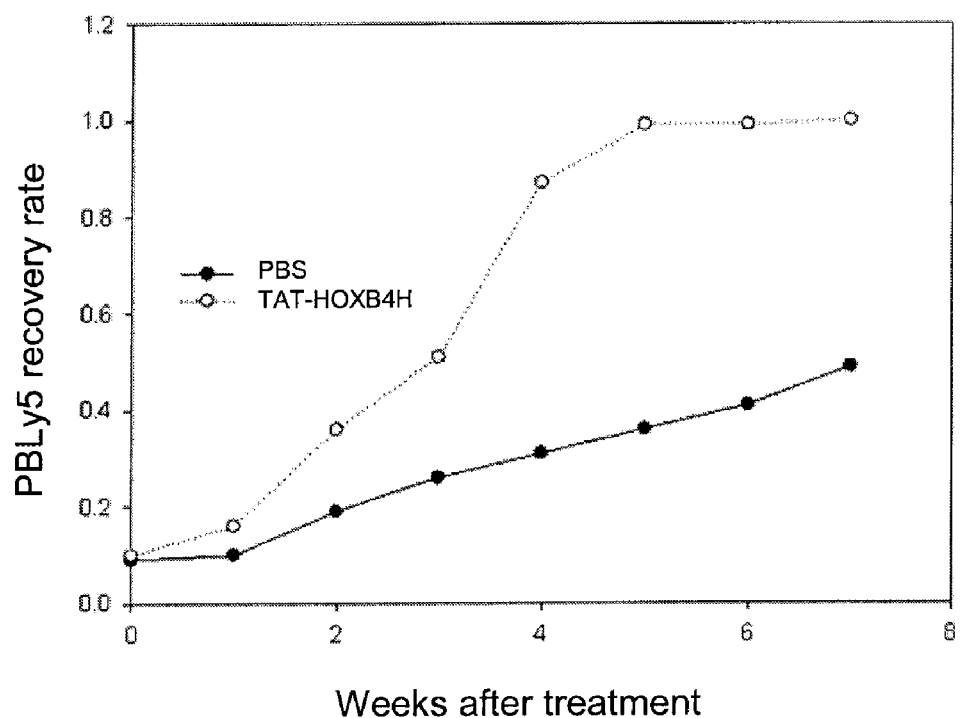
FIG. 11 shows effect of TAT-HOXB4H protein on hematopoietic recovery in Balb/c mice after cisplatin chemotherapy.

Effect of Recombinant TAT-HOXB4H Protein on Hematopoietic Recovery in NOD-SCID Mice $10^4$ human Lin−/CD34+ cells were injected into irradiated (2.5 Gy) NOD-LtSz-scid/scid (NOD-SCID) mice, along with $10^5$ CD34− irradiated accessory cells. The mice are divided into two groups randomly: one group (n=28) was injected intravenously with 10 μg per kg BW of recombinant TAT-HOXB4H protein twice per day, and the other (n=28) received PBS twice per day. The presence of human CD45+ cells in the peripheral blood cells of all mice was measured periodically by flow cytometry after transplantation. Hematopoietic recovery was evaluated as the number of mice whose human CD45+ cells reached levels of >0.1% in peripheral blood (PB) after transplantation. As shown in FIG. 10, improved hematopoietic recovery was observed in the mice injected with recombinant TAT-HOXB4H protein.

Example 9

Figure 8:
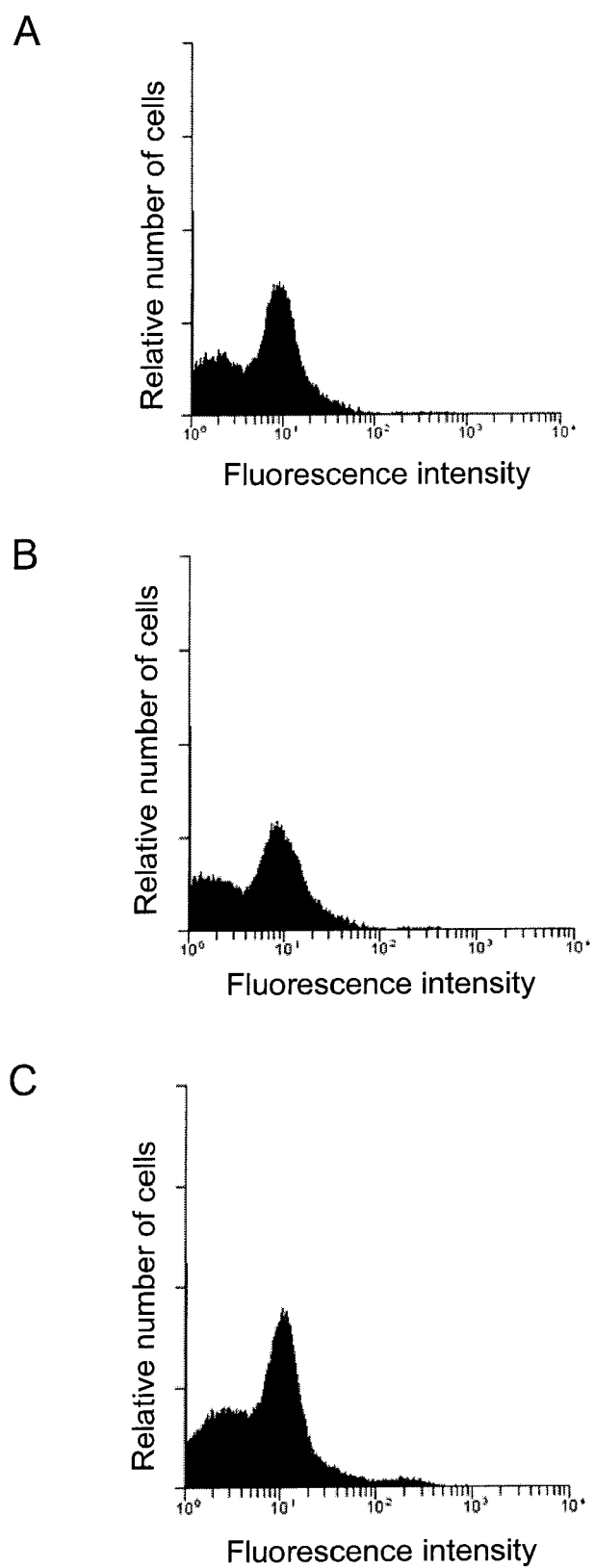
FIG. 8A shows the stimulatory effect of G-CSF on the number of CD34+ stem cells in bone marrow of mice analyzed by a flow cytometer.
FIG. 8B shows the effect of PBS on the number of CD34+ stem cells in bone marrow of mice analyzed by a flow cytometer.
FIG. 8C shows the stimulatory effect of TAT-HOXB4H on the number of CD34+ stem cells in bone marrow of mice analyzed by a flow cytometer.
Figure 9:
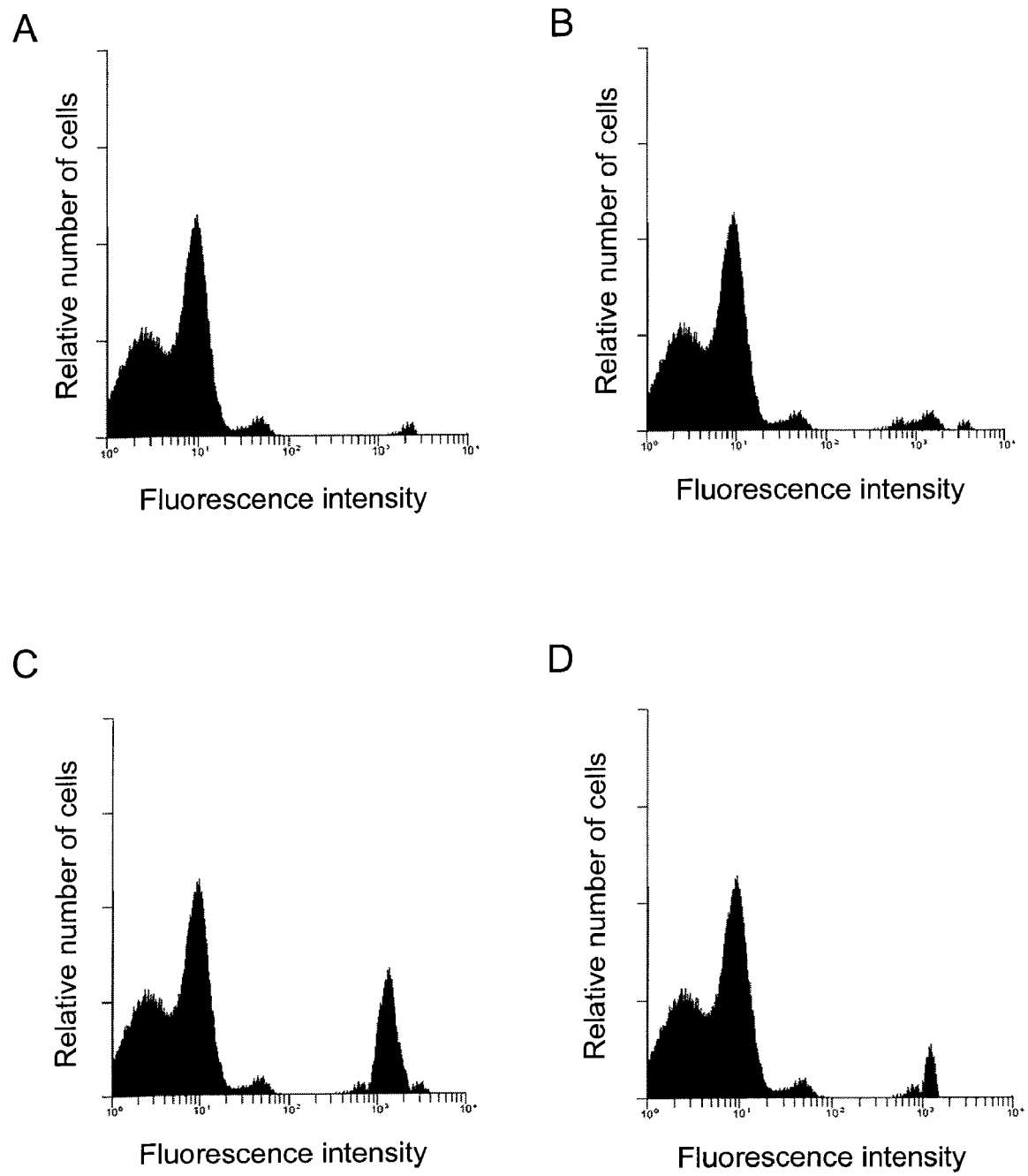
FIG. 9A shows the stimulatory effect of G-CSF on the number of CD34+ stem cells in bone marrow of rhesus monkey analyzed by a flow cytometer.
FIG. 9B shows the stimulatory effect of TAT-HOXB4H together with G-CSF on the number of CD34+ stem cells in bone marrow of rhesus monkey analyzed by a flow cytometer.
FIG. 9C shows the stimulatory effect of TAT-HOXB4H on the number of CD34+ stem cells in bone marrow of rhesus monkey analyzed by a flow cytometer.
FIG. 9D shows the effect of PBS on the number of CD34+ stem cells in bone marrow of rhesus monkey analyzed by a flow cytometer.

Effect of Recombinant TAT-HOXB4H Protein on Hematopoietic Recovery in Balb/c Mice After Cisplatin Chemotherapy 5 week-old Balb/c mice were repeatedly injected intravenously with cisplatin until the number of Ly5(murine CD45) cells in peripheral blood of the mice decreased to approximately 10% of the original number. The mice treated with cisplatin are divided into two groups randomly: one group (n=28) was injected intravenously with 10 μg per kg BW of recombinant TAT-HOXB4H protein twice per day, and the other (n=28) received PBS twice per day. The presence of Ly5 cells in the peripheral blood cells of all mice was measured periodically by flow cytometry after transplantation. Hematopoietic recovery rate was evaluated as the percentage of the number of Ly5 cells in peripheral blood to the original number. As shown in FIG. 8, improved hematopoietic recovery was observed in the mice injected with recombinant TAT-HOXB4H protein.

The animal models used in these experiments have been recognized in the art as predictive of results that will be obtained in human patients. See, e.g., Broxmeyer et al. (2005) *The Journal of Experimental Medicine*, 201, 1307-1318; Larochelle et al. (2006) *Blood* 107, 3772-3778.

Although the invention has been explained in relation to its various embodiments, it is to be understood that many other possible modifications and variations can be made without departing from the spirit and scope of the invention as hereinafter claimed.

What is claimed is:

1. A method for enhancing the mobilization of hematopoietic stem cells from bone marrow to peripheral blood, comprising:
   a) administering to a subject in need thereof an effective amount of a TAT-HOXB4H protein having the amino acid sequence of SEQ ID NO:4, wherein the protein increases the absolute number of hematopoietic stem cells in the bone marrow of the subject and is produced by a method comprising:
      (1) providing an isolated host cell comprising a vector encoding the protein;
      (2) expressing the protein in the host cell;
      (3) collecting an impure solution of the expressed protein;
      (4) purifying the protein from the impure solution by:
         (i) applying the impure solution to a chromatography column for purifying histidine-tagged proteins;
         (ii) washing the chromatography column for purifying histidine-tagged proteins with a washing buffer;
         (iii) eluting the protein from the chromatography column for purifying histidine-tagged proteins with an eluting buffer to form a partially purified protein solution;
         (iv) applying the partially purified protein solution to a cation ion exchange chromatography column;
         (v) washing the cation ion exchange chromatography column with a washing buffer; and
         (vi) eluting the purified protein from the cation ion exchange chromatography column in denatured form with an eluting buffer;
      (5) refolding the eluted denatured protein using hydrophobic compounds by:
         (i) combining the eluted denatured protein and a solution of hydrophobic compounds to form a solution of the protein and hydrophobic compounds;
         (ii) desalting the solution of the protein and hydrophobic compounds to obtain a desalted protein and hydrophobic compound solution;

(iii) removing the hydrophobic compounds from the desalted protein and hydrophobic compound solution using ultrafiltration by a centrifugal filter tube or a stir-cell;
(6) storing the purified protein in Dulbecco's modified eagle medium (DMEM); and
b) allowing the TAT-HOXB4H protein to increase the absolute number of hematopoietic stem cells in the bone marrow of the subject thereby enhancing the mobilization of hematopoietic stem cells to the peripheral blood of the subject.

2. The method of claim 1, wherein the subject in need thereof is a hematopoietic stem cells donor.

3. The method of claim 1, wherein the subject in need thereof is a patient having undergone autologous hematopoietic stem cells transplantation.

4. The method of claim 1, wherein the subject in need thereof is a granulocyte-colony stimulating factor-insensitive patient.

5. The method of claim 4, wherein the subject suffers from diseases caused by inherited hematopoietic stem cells deficiency.

6. The method of claim 5, wherein the subject suffers from inherited aplastic anemia.

7. A method for improving the recovery time of a patient having undergone hematopoietic stem cells transplantation, irradiation or chemotherapy comprising:
a) administering to a subject in need thereof, an effective amount of a TAT-HOXB4H protein having the amino acid sequence of SEQ ID NO:4, wherein the protein increases the absolute number of hematopoietic stem cells in the bone marrow of the subject and is produced by a method comprising:
(1) providing an isolated host cell comprising a vector encoding the protein;
(2) expressing the protein in the host cell;
(3) collecting an impure solution of the expressed protein;
(4) purifying the protein from the impure solution by:
(i) applying the impure solution to a chromatography column for purifying histidine-tagged proteins;
(ii) washing the chromatography column for purifying histidine-tagged proteins with a washing buffer;
(iii) eluting the protein from the chromatography column for purifying histidine-tagged proteins with an eluting buffer to form a partially purified protein solution;
(iv) applying the partially purified protein solution to a cation ion exchange chromatography column;
(v) washing the cation ion exchange chromatography column with a washing buffer; and
(vi) eluting the purified protein from the cation ion exchange chromatography column in denatured form with an eluting buffer;
(5) refolding the eluted denatured protein using hydrophobic compounds by:
(i) combining the eluted denatured protein and a solution of hydrophobic compounds to form a solution of the protein and hydrophobic compounds;
(ii) desalting the solution of the protein and hydrophobic compounds to obtain a desalted protein and hydrophobic compound solution;
(iii) removing the hydrophobic compounds from the desalted protein and hydrophobic compound solution using ultrafiltration by a centrifugal filter tube or a stir-cell;
(6) storing the purified protein in Dulbecco's modified eagle medium (DMEM); and
b) allowing the TAT-HOXB4H protein to increase the absolute number of hematopoietic stem cells to the bone marrow of the subject.

8. The method of claim 7, wherein the subject in need thereof is a hematopoietic stem cells donor.

9. The method of claim 7, wherein the subject in need thereof is a patient having undergone autologous hematopoietic stem cells transplantation.

10. The method of claim 7, wherein the subject in need thereof is a granulocyte-colony stimulating factor-insensitive patient.

11. The method of claim 10, wherein the subject suffers from diseases caused by inherited hematopoietic stem cells deficiency.

12. The method of claim 11, wherein the subject suffers from inherited aplastic anemia.

13. A method for enhancing the mobilization of hematopoietic stem cells from bone marrow to peripheral blood, comprising:
a) administering to a subject in need thereof an effective amount of a TAT-HOXB4 protein having the amino acid sequence of positions 8 to 273 of SEQ ID NO:4, wherein the protein increases the absolute number of hematopoietic stem cells in the bone marrow of the subject and is produced by a method comprising:
(1) providing an isolated host cell comprising a vector encoding the protein with a histidine tag (His-tag) at the N-terminus, the C-terminus, or both the N- and C-terminus of the protein;
(2) expressing the protein in the host cell;
(3) collecting an impure solution of the expressed protein;
(4) purifying the protein from the impure solution by:
(i) applying the impure solution to a chromatography column for purifying histidine-tagged proteins;
(ii) washing the chromatography column for purifying histidine-tagged proteins with a washing buffer;
(iii) eluting the protein from the chromatography column for purifying histidine-tagged proteins with an eluting buffer to form a partially purified protein solution;
(iv) applying the partially purified protein solution to a cation ion exchange chromatography column;
(v) washing the cation ion exchange chromatography column with a washing buffer; and
(vi) eluting the purified protein from the cation ion exchange chromatography column in denatured form with an eluting buffer;
(5) refolding the eluted denatured protein using hydrophobic compounds by:
(i) combining the eluted denatured protein and a solution of hydrophobic compounds to form a solution of the protein and hydrophobic compounds;
(ii) desalting the solution of the protein and hydrophobic compounds to obtain a desalted protein and hydrophobic compound solution;
(iii) removing the hydrophobic compounds from the desalted protein and hydrophobic compound solution using ultrafiltration by a centrifugal filter tube or a stir-cell;
(6) removing a His-tag from at least one end of the protein, and
(7) storing the purified protein in Dulbecco's modified eagle medium (DMEM); and b) allowing the TAT-HOXB4 protein to increase the absolute number of hematopoietic stem cells in the bone marrow of the subject thereby enhancing the mobilization of hematopoietic stem cells to the peripheral blood of the subject.

14. A method for improving the recovery time of a patient having undergone hematopoietic stem cells transplantation, irradiation or chemotherapy comprising:
   a) administering to a subject in need thereof, an effective amount of a TAT-HOXB4 protein having the amino acid sequence of positions 8 to 273 of SEQ ID NO:4, wherein the protein increases the absolute number of hematopoietic stem cells in the bone marrow of the subject and is produced by a method comprising:
   (1) providing an isolated host cell comprising a vector encoding the protein with a histidine tag (His-tag) at the N-terminus, the C-terminus, or both the N- and C-terminus of the protein;
   (2) expressing the protein in the host cell;
   (3) collecting an impure solution of the expressed protein;
   (4) purifying the protein from the impure solution by:
      (i) applying the impure solution to a chromatography column for purifying histidine-tagged proteins;
      (ii) washing the chromatography column for purifying histidine-tagged proteins with a washing buffer;
      (iii) eluting the protein from the chromatography column for purifying histidine-tagged proteins with an eluting buffer to form a partially purified protein solution;
      (iv) applying the partially purified protein solution to a cation ion exchange chromatography column;
      (v) washing the cation ion exchange chromatography column with a washing buffer; and
      (vi) eluting the purified protein from the cation ion exchange chromatography column in denatured form with an eluting buffer;
   (5) refolding the eluted denatured protein using hydrophobic compounds by:
      (i) combining the eluted denatured protein and a solution of hydrophobic compounds to form a solution of the protein and hydrophobic compounds;
      (ii) desalting the solution of the protein and hydrophobic compounds to obtain a desalted protein and hydrophobic compound solution;
      (iii) removing the hydrophobic compounds from the desalted protein and hydrophobic compound solution using ultrafiltration by a centrifugal filter tube or a stir-cell;
   (6) removing a His-tag from at least one end of the protein, and
   (7) storing the purified protein in Dulbecco's modified eagle medium (DMEM); and
   b) allowing the TAT-HOXB4 protein to increase the absolute number of hematopoietic stem cells to the bone marrow of the subject.

15. The method of claim 13, wherein the His-tag is removed from the N-terminus of the protein.

16. The method of claim 13, wherein the His-tag is removed from the C-terminus of the protein.

17. The method of claim 13, wherein the His-tag is removed from both the N- and C-terminus of the protein.

18. The method of claim 14, wherein the His-tag is removed from the N-terminus of the protein.

19. The method of claim 14, wherein the His-tag is removed from the C-terminus of the protein.

20. The method of claim 14, wherein the His-tag is removed from both the N- and C-terminus of the protein.

21. The method of claim 1, 7, 13 or 14, wherein the subject suffers from a hematological disorder and/or an immunological disorder.

* * * * *

SEQUENCE LISTING

```
<160> NUMBER OF SEQ ID NOS: 5

<210> SEQ ID NO 1
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
```

```
tatgcaccac caccaccacc actacggccg caagaaacgc cgccagcgcc gccggcg       57
```

<210> SEQ ID NO 2
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2

```
ctagcggcgc tggcggcgtt tcttgcggcc gtagtggtgg tggtggtggt gca           53
```

<210> SEQ ID NO 3
<211> LENGTH: 840
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
atgcaccacc accaccacca ctacggccgc aagaaacgcc gccagcgccg ccgcgctagc    60
atggctatga gttcttttt gatcaactca aactatgtcg accccaagtt ccctccatgc    120
gaggaatatt cacagagcga ttacctaccc agcgaccact cgcccgggta ctacgccggc   180
ggccagaggc gagagagcag cttccagccg gaggcgggct cgggcggcg cgcggcgtgc    240 accgtgcagc gctacgcggc ctgccgggac cctgggcccc gccgcctcc gccaccaccc    300 ccgccgcccc cgccaccgcc cggtctgtcc cctcgggctc ctgcgccgcc acccgccggg   360
gccctcctcc cggagcccgg ccagcgctgc gaggcggtca gcagcagccc ccgccgcct   420 ccctgcgccc agaaccccct gcaccccagc ccgtcccact ccgcgtgcaa agagcccgtc   480
gtctacccct ggatgcgcaa agttcacgtg agcacggtaa accccaatta cgccggcggg   540
gagcccaagc gctctcggac cgcctacacg cgccagcagg tcttggagct ggagaaggaa   600
tttcactaca accgctacct gacacggcgc cggagggtgg agatcgccca cgcgctctgc   660
ctctccgagc gccagatcaa gatctggttc cagaaccggc gcatgaagtg gaaaaaagac   720
cacaagttgc caacaccaa gatccgctcg gtggtgcgg caggctcagc cggagggccc    780
cctggccggc caatggagg ccccgcgcg ctcctcgagc accaccacca ccaccactga    840
```

<210> SEQ ID NO 4
<211> LENGTH: 279
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Met His His His His His His Tyr Gly Arg Lys Lys Arg Gln Arg
 1               5                  10                  15

Arg Arg Ala Ser Met Ala Met Ser Ser Phe Leu Ile Asn Ser Asn Tyr
                20                  25                  30

Val Asp Pro Lys Phe Pro Pro Cys Glu Glu Tyr Ser Gln Ser Asp Tyr
            35                  40                  45

Leu Pro Ser Asp His Ser Pro Gly Tyr Tyr Ala Gly Gly Gln Arg Arg
        50                  55                  60

Glu Ser Ser Phe Gln Pro Glu Ala Gly Phe Gly Arg Arg Ala Ala Cys
65                  70                  75                  80
```

```
Thr Val Gln Arg Tyr Ala Ala Cys Arg Asp Pro Gly Pro Pro Pro Pro
                 85                  90                  95

Pro Pro Pro Pro Pro Pro Pro Pro Pro Pro Gly Leu Ser Pro Arg
            100                 105                 110

Ala Pro Ala Pro Pro Pro Ala Gly Ala Leu Leu Pro Glu Pro Gly Gln
            115                 120                 125

Arg Cys Glu Ala Val Ser Ser Ser Pro Pro Pro Pro Cys Ala Gln
        130                 135                 140

Asn Pro Leu His Pro Ser Pro Ser His Ser Ala Cys Lys Glu Pro Val
145                     150                 155                 160

Val Tyr Pro Trp Met Arg Lys Val His Val Ser Thr Val Asn Pro Asn
                165                 170                 175

Tyr Ala Gly Gly Glu Pro Lys Arg Ser Arg Thr Ala Tyr Thr Arg Gln
            180                 185                 190

Gln Val Leu Glu Leu Glu Lys Glu Phe His Tyr Asn Arg Tyr Leu Thr
            195                 200                 205

Arg Arg Arg Arg Val Glu Ile Ala His Ala Leu Cys Leu Ser Glu Arg
        210                 215                 220

Gln Ile Lys Ile Trp Phe Gln Asn Arg Arg Met Lys Trp Lys Lys Asp
225                 230                 235                 240

His Lys Leu Pro Asn Thr Lys Ile Arg Ser Gly Gly Ala Ala Gly Ser
                245                 250                 255

Ala Gly Gly Pro Pro Gly Arg Pro Asn Gly Gly Pro Arg Ala Leu Leu
            260                 265                 270

Glu His His His His His His
        275

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

<400> SEQUENCE: 5

His His His His His His
 1               5
```